United States Patent [19]
Chivers

[11] Patent Number: 5,459,564
[45] Date of Patent: Oct. 17, 1995

[54] APPARATUS AND METHOD FOR INSPECTING END FACES OF OPTICAL FIBERS AND OPTICAL FIBER CONNECTORS

[76] Inventor: James T. Chivers, 3212 N. 27th St., Phoenix, Ariz. 85016

[21] Appl. No.: 198,997

[22] Filed: Feb. 18, 1994

[51] Int. Cl.[6] ............................. G01B 9/02; G01N 21/88
[52] U.S. Cl. ........................................ 356/73.1; 356/359
[58] Field of Search .................................. 356/73.1, 359, 356/360

[56] References Cited

U.S. PATENT DOCUMENTS

| 5,064,286 | 11/1991 | Ai et al. | 356/153 |
| 5,112,129 | 5/1992 | Davidson et al. | 356/359 |

FOREIGN PATENT DOCUMENTS

| 63-285452 | 11/1988 | Japan | 356/359 |

OTHER PUBLICATIONS

OPTISPEC®, Fiber Inspection Systems, Zoom in on Quality, Micro Enterprises, Inc.
Optical Fiber Micro–Interferometer F–IM1/F–IM2 Instruction Manual, Newport Corporation.
Cleave–Chek Interferometer System, Technical Data, Norland.
Connect–Chek Interferometer System, Technical Data, Norland.

Primary Examiner—Vincent P. McGraw
Attorney, Agent, or Firm—Cahill, Sutton & Thomas

[57] ABSTRACT

An inspection and measurement device including an interferometer with a parfocal, parcentral zoom lens is adapted to inspect and measure an end surface of an optical fiber or connector. With the optical fiber or connector supported on an xyz stage, the interferometer is set to a "microscope" mode. Controls of the xyz stage are adjusted to bring the end surface into focus and alignment with the optical axis of the interferometer. The interferometer is set to operate in an interference mode, causing display of a fringe pattern resulting from interference of a test beam with a reference beam. The z control is adjusted slightly, if required, to optimize the contrast of the displayed fringe pattern. The zoom lens then is operated to change magnification of the fringe pattern so as to obtain an optimum number of available fringes across a selected portion of the end surface without refocusing or realigning the end surface with the focal point of the zoom lens. A tilt stage can support the optical fiber or connector, orienting it so as to facilitate measurement of an angle on the end surface or protrusion or undercut of fiber with respect to the ferrule of a connector without any readjustment of the xyz stage.

14 Claims, 2 Drawing Sheets

APPARATUS AND METHOD FOR INSPECTING END FACES OF OPTICAL FIBERS AND OPTICAL FIBER CONNECTORS

BACKGROUND OF THE INVENTION

The invention relates to an apparatus and method for inspection, quantitative testing, and/or topographic analysis of ends of optical fibers and optical connectors, and more particularly to a system and method utilizing an inexpensive interferometer including an electronically controlled parcentral, parfocal zoom objective lens to allow rapid changing of magnification so as to display an optimum number of available fringes of the interferogram without refocusing.

Use of optical fibers in various data communication systems and various optical devices has increased greatly over the past decade. Consequently, the need for measuring and testing the quality of optical fibers and optical connectors also has grown rapidly. The end faces of optical fibers and optical connectors must be of extremely high quality and very low deviation from optimum shape to prevent misalignments, air gaps, reflections or scattering of light at interfaces at which optical fibers need to be coupled in an optical fiber link. These imperfections are compounded by being summed with similar imperfections at all other fiber junctions in the system and ultimately can lead to greatly increased light attenuation, lower signal-to-noise ratios, and significantly lower system bandwidth.

Several low cost interferometer-based systems for inspecting optical fibers and optical connectors are available, including the CLEAVE-CHECK system and the CONNECT-CHEK system manufactured and marketed by Norland Products, Inc. of New Brunswick, N.J., the F-IM1 and F-IM2 interferometer systems for measuring the cleave angle and surface quality of an optical fiber end face marketed by Newport Corporation of Fountain Valley, Calif. and the Optispec Inspection system marketed by Micro Enterprises, Inc. of Norcross, Ga.

All of the above fiber inspection systems are less flexible and less accurate than desirable, and their utilization is more time consuming than desirable. The magnification of the above interferometer devices can be changed only by selecting a different fixed objective lens, and when this is done the interferometer must be refocused, and, usually the x,y alignment of the fiber or connector end surface also must be adjusted.

Although xy adjustment is required to truly center the sample after changing fixed objectives, this is very difficult to accomplish on the prior art devices, as only very crude adjustment techniques (if any) are provided for making such adjustments. The Newport and Micro Enterprise Systems inspection devices do not provide any accurate xy adjustment during their measurement sequences. On the Norland system a plate holding the sample is physically shifted by hand and locked down using two thumb screws when re-centering has been accomplished. Because of the foregoing lack of accurate xy adjustment capability, the prior art systems often do not use all of the available area on the screen of the display monitor to allow for such offsets, and thereby compromise data quality and visibility of fringes.

Each of the above mentioned operations is quite time-consuming. Inspection and measurement of various optical fiber or optical connector end faces usually necessitates use of various magnifications to first locate the sample, and then to obtain an optimum number of interference fringes within the field of view of the interferometer, if maximum accuracy of the measurement is to be achieved.

The economic realities of optical fiber and optical connector inspection systems dictate that they be relatively inexpensive. As a practical matter, fiber and/or connector inspection and measurement systems usually should cost less than approximately $10,000.00. This requirement prevents more expensive, sophisticated, commercially available interferometers (such as the Wyko 6000 described in U.S. Pat. No. 5,064,286, which costs roughly $50,000.00 or more) from being suitable for optical fiber and optical connector inspection applications. Zoom microscope objectives have been used in interferometers (such as the Wyko 6000) which are much more expensive and sophisticated than those used in fiber and connector inspection systems, but it is economically and technically unfeasible to adapt such interferometers for use in fiber and connector inspection systems.

Recent developments in the transmission and receiving ends of a fiber link have meant that the fiber and/or fiber connectors are likely to be the weakest link in achieving extremely high bandwidth fiber optic systems (especially for cable television systems and the like). This hurdle has led to the development of "super-polished" connectors, angled polished connectors and angled fiber cleaves. As tolerances are tightened and angles are purposely added, the task of measuring optical fibers and connectors becomes more difficult and far less tolerant of equipment error. Ensuring that two angled polished connectors will physically mate to within approximately a 1 micron tolerance is very difficult, but this is what is required to meet the needs of present high bandwidth fiber optic systems.

Furthermore, engineers now are placing far tighter tolerance requirements on "undercutting" or "overpolishing" of the end faces of optical fibers within optical connectors, wherein the fiber portion of an optical connector polishes more easily than the surrounding ferrule. This effect, however small, can produce an air gap between adjoining end faces, thereby reducing system bandwidth. The ability to measure both undercutting and equally undesirable (but less likely) protrusion of the optical fiber with respect to the connector end surface is becoming more essential as the technology of fiber optic links progresses.

It should be appreciated that approximately 70 fringes is the maximum number that can be readily resolved on an ordinary monitor. Using a conventional spherical FC/PC connector as an example, the same number of "available" fringes always will exist if the radius of curvature of the connector end surface within the field of view is below a certain value. In effect, more fringes actually are "available" than can be resolved on the monitor.

It should be appreciated that various standards and machines are used to polish connector ends, and the fixed objective systems of the prior art are never able to "see" the "optimum" number of the available fringes on all types of connector end surfaces to be tested. This effectively reduces the quality of the raw data of the prior art systems, which may lead to acceptance of lower quality optical connector end surfaces, and hence can lead to higher attenuation, lower bandwidth and lower signal to noise ratios in the optical systems made from such components.

It is difficult to overemphasize the importance of increased accuracy of measurement/testing of optical fiber and optical connector end surfaces in the overall effort to improve the quality of optical fiber interconnections and ultimately obtaining lower loss and higher bandwidth systems.

For at least the past decade, there has been a recognized but unmet need for a substantially improved but nevertheless inexpensive optical fiber and connector inspection and measurement system which provides substantially greater accuracy and substantially faster operation than has been achievable by use of the above mentioned commercially available fiber and/or connector inspection systems.

SUMMARY OF THE INVENTION

Accordingly, it is an object of the invention to provide an inexpensive fiber and connector inspection and measurement system and method which is much more accurate than the above described prior art fiber and/or connector inspection systems.

It is another object of the invention to provide an inexpensive fiber and connector inspection and measurement system and method which is much faster in overall operation than the fiber inspections of the prior art.

It is another object of the invention to provide an inexpensive fiber and connector inspection and measurement system which is much easier to use than those of the prior art, and is capable of inspection/measurement of virtually any optical connector, angled polished connector, protrusion or undercut condition, fiber cleave, angled fiber cleave, or ribbon fiber.

It is another object of the invention to provide a fiber/connector inspection/measurement system of the type described which requires low maintenance, and especially requires very little cleaning of internal optical surfaces.

It is another object of the invention to provide an inexpensive fiber/connector inspection/measurement system and method which is readily adaptable to computer control and computer image analysis.

Briefly described, and in accordance with one embodiment thereof, the invention provides an inspection and measurement device including an interferometer to inspect and measure the topography of an end surface of an optical fiber or optical connector. The interferometer includes a light emitting diode, a beam splitter, a reference surface, a zoom microscope objective, and a CCD camera coupled to a display monitor. The optical fiber or optical connector is mounted and securely supported on an xyz stage. The interferometer is set to operate in a "microscope mode". A z control of the xyz stage is adjusted slightly to move the sample end surface to the focal point of a parfocal, parcentral zoom lens included in the interferometer. If necessary, x and y controls of the xyz stage are adjusted to align an image of the end surface, displayed on the monitor to the center of the field of view of the zoom lens. The interferometer is set to operate in an interference mode, causing a fringe pattern resulting from interference of a test beam reflected from the end surface with a reference beam reflected from the reference surface to be displayed on the monitor. The z control is adjusted slightly, if necessary, to optimize the contrast of the displayed fringe pattern. The zoom lens then is operated to change magnification of the fringe pattern so as to obtain an optimum number of available fringes across a selected portion of the end surface without refocusing or realigning the end surface with the central point of the zoom lens. The relatively large number of "available" fringes across the selected portion of the end surface allows very accurate determination of the sample topography. The xyz stage of the interferometer can include a tilt stage for supporting the optical fiber or connector, wherein an angle of the tilt stage is accurately adjusted so as to facilitate measuring an angle on the sample end surface without any adjustment of the x and y controls to re-center the image, and only minimal (if any) adjustment of the z control to optimize the focus. The same stage can be used to indicate either protrusion or undercut of the optical fiber with respect to the end surface of an optical connector.

DETAILED DESCRIPTION OF THE PREFERRED EMBODIMENTS

Figure 1:
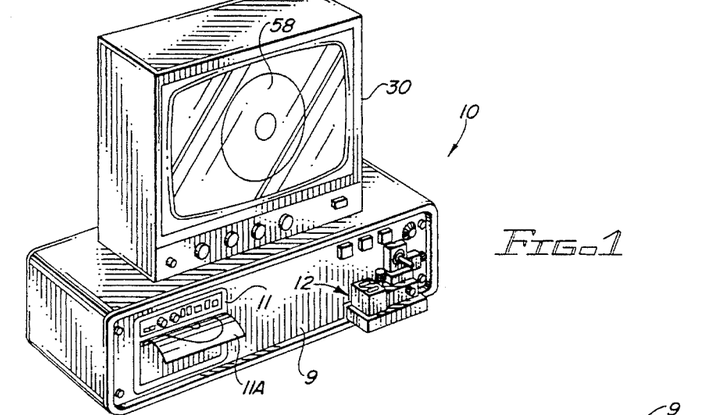
FIG. 1 is a perspective view of a preferred embodiment of the invention.
Figure 1A:
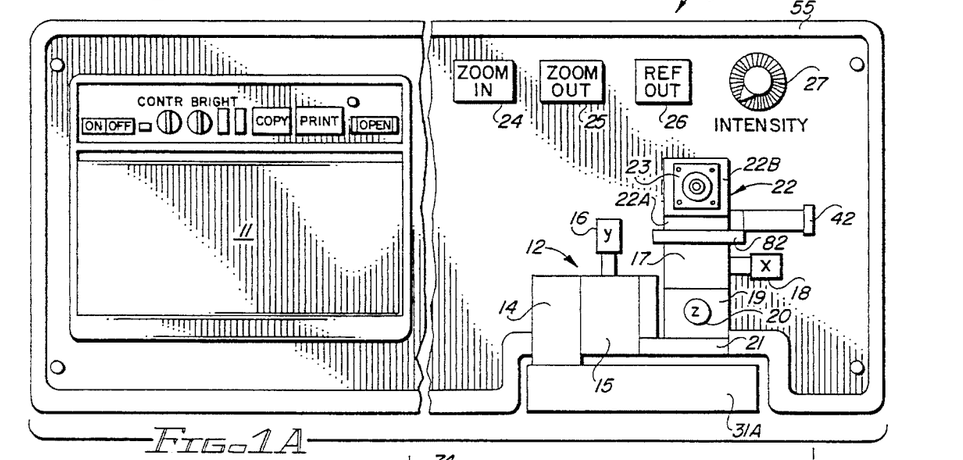
FIG. 1A is a detailed diagram of the front panel of the fiber inspection system of FIG. 1.

Referring to FIGS. 1 and 1A, optical fiber and connector inspection and measurement system 10 includes an interferometer/stage assembly 9 and a monitor 30. Interferometer/stage assembly 9 (hereinafter referred to as interferometer unit 9) includes an xyz stage 12.

A suitable chuck assembly 23 (see FIG. 3B) for holding an optical connector 67 (see FIG. 3D) is attached directly to a mounting surface of a "tilt stage" 22 such that the end surface of the sample (an optical connector) falls precisely at the center of rotation 74 (FIG. 3B) of tilt stage 22. Tilt stage 22 is pivotally mounted on a top mounting surface of a mounting plate 82, which is squarely and securely attached to the top mounting surface of x translator 17. Mounting plate 82 also supports tilt stage micrometer 42, more clearly shown in FIG. 2. A different chuck 23A, shown in FIG. 3A, is used to hold an optical fiber 68 so its end face is at rotational axis 74. A typical optical fiber has a diameter of 125 microns. The ferrule 72 (see FIG. 3D) of a typical optical fiber connector typically has a diameter of 2500 microns.

Interferometer unit 9 also includes a "ZOOM IN" push button switch 24, a "ZOOM OUT" push button switch 25, a (REF OUT) push button switch 26, and a rotary LED intensity control 27. Interferometer unit 9 also includes an optional printer 11, which can be a Sony model UP860.

xyz stage 12 is rigidly mounted on a front extension 31A of a base plate 31 by means of post 14, which is subsequently described with reference to FIGS. 1A and 2. xyz stage 12 includes x translator 17, y translator 15, and z translator 19. xyz stage 12 can be constructed of three conventional manually adjustable translator assemblies. Bracket 21 is connected to the stage of y translator 15 to support z translator 19 and x translator 17.

Movement of tilt stage 22 and the sample carried thereby in the z direction to focus the end surface image is accomplished by rotating micrometer control knob 20. Movement of tilt stage 22 and the sample carried thereby in the x and y directions to align the end surface of the optical fiber or optical connector being inspected or measured with the optical axis of the interferometer is controlled by rotating micrometer knobs 18 and 16, respectively.

Figures 2, 3C, 3D, 4:
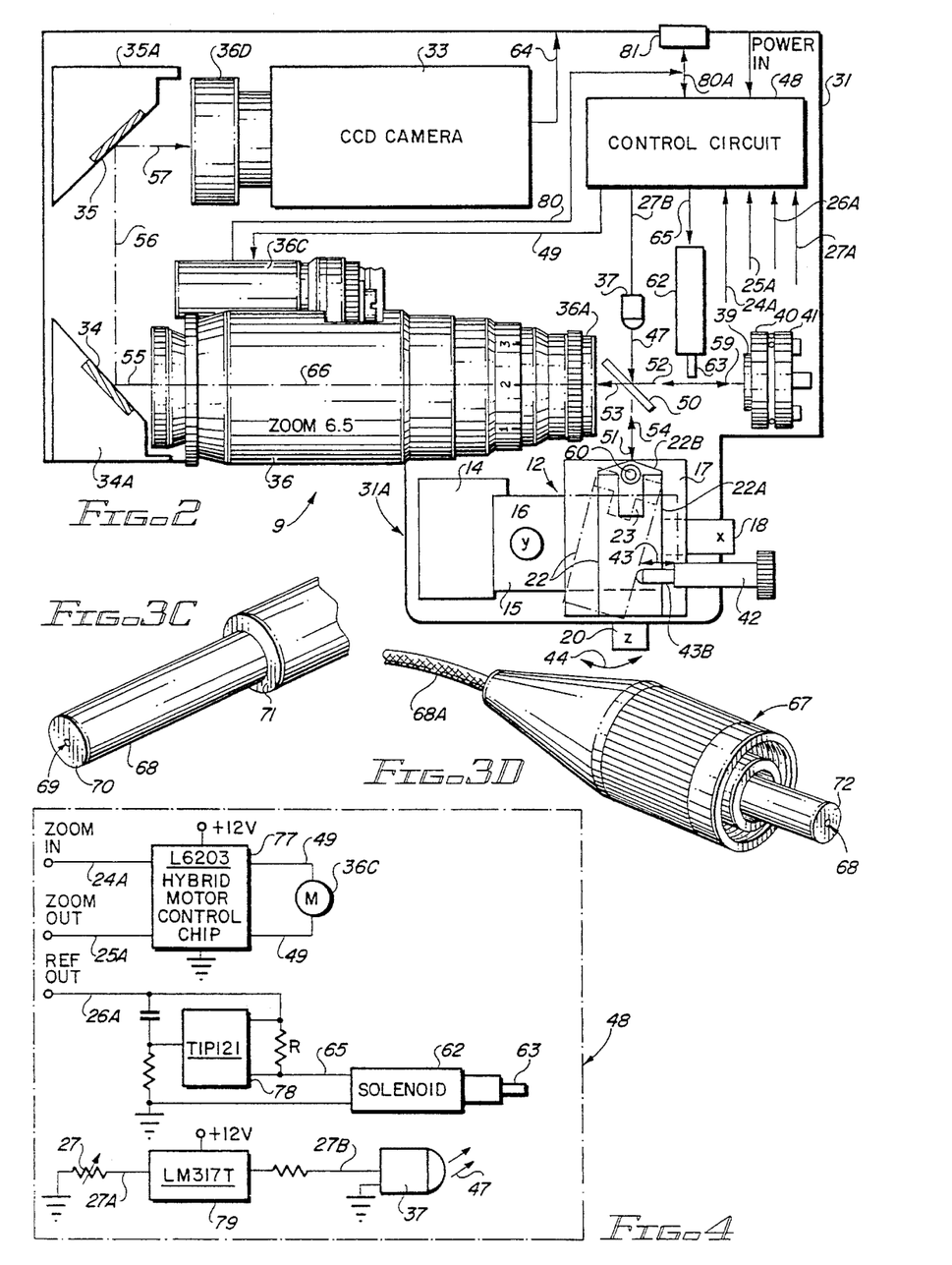
FIG. 2 is a plan view diagram illustrating the components of the interferometer and test chuck assembly of the system shown in FIGS. 1 and 1A.
FIG. 3C is a perspective view of an optical fiber.
FIG. 3D is a perspective view of an optical connector.
FIG. 4 is a schematic diagram of control circuit 48, which was designed to provide virtually instant braking of the motor of zoom lens 36, so that when the zoom buttons are released, the motor stops instantly, rather than continuing to change magnification due to built-up motor inertia.
Figure 3A:
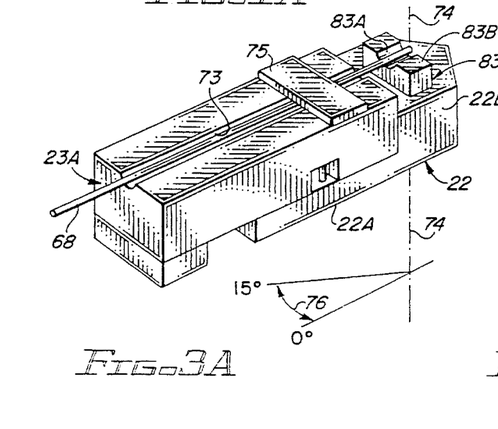
FIG. 3A is a perspective view of a chuck holding an optical fiber.

As shown in FIGS. 1A and 2 tilt stage 22 includes a horizontal base member 22A which is pivotally connected by pivot pin 60 to the top mounting surface of mounting plate 82. Tilt stage 22 also includes a vertical end section 22B having a recess 22C (FIG. 3B) therein. Optical connector chuck assembly 23 is mounted on a vertical surface at the "bottom" of recess 22C. The depth of recess 22C is precisely manufactured so that the end of ferrule 72 (FIG. 3D) of an inserted optical connector 67 lies precisely at the center 74 of pivot pin 60 (FIG. 2), the location of which is adjusted in the z direction to be at the focal point of zoom lens 36. Thus, any tilt applied to tilt stage 22 and hence to optical connector 67 supported thereby will have virtually no effect on the xyz position of the end surface of optical connector 67.

Figure 3B:
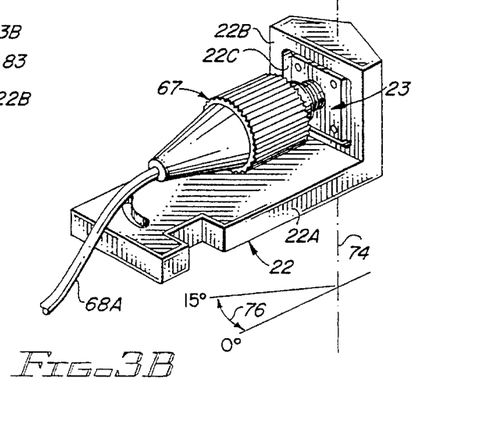
FIG. 3B is a perspective view of a chuck holding an optical connector.

Referring to FIG. 3A, an optical fiber chuck 23A can be attached to the horizontal surface of a modified version of tilt stage 22 wherein the height of vertical end section 22B is substantially lower than for the version shown in FIG. 3B. Optical fiber chuck 23A has a precision V groove 73 in its upper surface for supporting optical fiber 68.

An alignment element 83 is attached to the top surface of vertical end section 22B of tilt stage 22. Alignment element 83 has a deep recess 83A therein, which allows the sample end of optical fiber 68 to extend to pivot axis 74 without any danger of touching any portion of alignment element 83. A vertical face 83B of alignment element 83 on its side opposite to optic fiber chuck 23A is perpendicular to the optical axis of fiber 68 and is precisely aligned with rotation axis 74. As subsequently explained, a portion of that surface of alignment element 83 appears peripherally within the field of view of zoom lens 36 when z control 20 has been operated to bring that vertical surface 83B, and hence rotation axis 74, into perfect alignment with the focal point of zoom lens 36.

The sample end surface of optical fiber 68 is aligned with the center axis 74 of pivot pin 60. A magnetic pad 75 placed on the top surface of chuck 23A holds optical fiber 68 securely in place while allowing optical fiber 68 to be axially rotated or pulled back.

FIG. 3C illustrates a typical optical fiber 68, which includes cladding 70 that provides physical strength for the fiber and a central light conducting portion 69 known as the "core". Numeral 71 designates a "primary coating" layer that typically is 250 microns in diameter. Optical fiber 68 is cut by a "cleaver", producing an end surface known as a "cleave", which may be perpendicular to the optical axis of the fiber, or may be at a small "cleave angle" which typically is 8 degrees from perpendicular, thereby preventing back reflection.

FIG. 3D illustrates a typical optical connector 67. An optical fiber 68 within "jacketed" fiber 68A extends through a precision hole in ferrule 72 of optical connector 67, as indicated by numeral 68 in FIG. 3D.

It should be recognized that optical fiber 68 within ferrule 72 often has a core diameter of only 8 microns, which is very small compared to the usual 2500 micron diameter of ferrule 72. Obviously, the eight micron optical fiber core 69 (FIG. 3C) which must be coupled by an optical connector to another optical fiber core within another optical connector by means of a standard connector coupler (not shown) must be very precisely aligned thereto, such that the alignment error is no more than approximately one micron in order to avoid appreciable losses in light transmission between the optical connectors. This is the reason that there is a great need for extreme accuracy in the manufacture and testing/inspection of end surfaces of optical fibers and optical connectors, to assure adequate quality control procedures.

As shown in FIG. 2, interferometer unit 9 includes a base plate 31 which is covered by a generally dustproof housing 55 (FIG. 1), except for the front base plate portion 31A which supports xyz stage 12.

A Michelson interferometer included within interferometer unit 9 includes CCD camera 33 (which can be a model XC73, available from Sony, of California), an electronically controlled zoom lens 36 (which can be a model Zoom 6000, available from Navitar of Rochester, N.Y.), a 2X sub lens 36A, a suitable light emitting diode 37, a beam splitter 50 (which can be an ordinary pellicle) and a reference mirror 39 supported on a "theta-phi" mirror mount 40,41. Zoom lens 36 is parfocal (meaning that its focal length does not change in the "z" direction along its optical axis as its magnification is changed) and parcentral (meaning that the image being magnified does not shift laterally in the x or y directions as its magnification is changed).

A pair of 45° inclined fold mirrors 34 and 35 are mounted on support posts 34A and 35A, respectively, which are attached to base plate 31. Suitable mounts (not shown) attach CCD camera 33 and zoom lens 36 to base plate 31. Reference mirror support 40,41 is indirectly attached to base plate 31.

Control circuit 48, details of which are shown in FIG. 4, receives "ZOOM IN" control signal 24A, "ZOOM OUT" control signal 25A, REF OUT (reference out) control signal 26A, and intensity control signal 27A from controls 24, 25, 26, and 27 on the front panel (FIG. 1A) of interferometer unit 9, respectively.

Referring to FIG. 4, control circuit 48 includes an L6203 hybrid motor control chip 77, available from Maplins of Great Britain. Chip 77 receives ZOOM IN and ZOOM OUT inputs 24A and 25A and produces zoom control signals via conductors 49 to zoom motor 36C of zoom lens 36. Hybrid motor control chip 77 contains all of the electronics required to move zoom motor 36C backward and forward in response to ZOOM IN and ZOOM OUT commands 24A and 25A, respectively. It also contains circuitry to bring zoom motor 36C to an almost immediate stop when either command button 24A or 25A is released. Control circuit 48 also includes a TIP121 power Darlington transistor connected as shown to provide a high initial current pulse followed by a smaller holding current to solenoid 62 via conductor 65 in response to REF OUT signal 26A. When REF OUT signal 26A is applied, power transistor TIP121 short circuits resistor R for a few hundred milliseconds to allow solenoid 62 sufficient current to retract element 63. After this time, resistor R is returned to the circuit to prevent excessive heat dissipation in the event solenoid 62 remains actuated for prolonged periods. Control circuit 48 also includes an LM317T variable voltage regulator chip 79 which receives intensity control signal 27A from intensity control potentiometer 27 and generates intensity control signal 27B to light emitting diode 37.

As indicated above, control circuit 48 controls zoom motor 36C to thereby increase or decrease the magnification of zoom lens 36. The change in magnification occurs without changing the focal point thereof, as zoom lens 36 is a parfocal, parcentral zoom lens with a magnification range from 0.7 to 6.5, which also is multiplied by a 2X extender lens 36A. The parcentral accuracy of zoom lens 36 is only a few microns over its entire magnification range.

A control line 80 extends from zoom lens 36 to a connector 81 on the rear panel of interferometer unit 9 and carries positional information indicating the present magnification of zoom lens 36. This information is used for automated fringe analysis which can be performed by a computer connected to interferometer unit 9. The zoom positional information indicates the present true field of view in the form of a proportional voltage signal. Interface line 80A also carries additional conductors for ZOOM IN signal 24A, ZOOM OUT signal 25A, intensity control signal 27A, and REF OUT signal 26A which, when combined with video signal 64, allows complete computer control of interferometer unit 9 and analysis of data received therefrom and display of the results of such analysis.

Control circuit 48 also produces an intensity control signal 27B to control the intensity of light emitting diode (LED) 37. LED 37 produces beam 47, the intensity of which usually should be increased as the magnification of zoom lens 36 is increased. LED 37, which inherently is quasimonochromatic, that is, of narrow spectral width, preferably has a center wavelength of 570 to 900 nanometers, so that a relatively low cost CCD camera 33 can be used. (A laser source also could be used.) LED beam 47 is partly reflected by pellicle 50 to produce beam 59. Beam 59 is reflected from the reference surface 39 to produce beam 52, which passes through pellicle 50 into the objective lens of zoom lens 36. The remaining portion of LED beam 47 is transmitted through pellicle 50 as beam 51 to the "test surface" of the optical fiber or optical connector end surface mounted on tilt assembly 22. Beam 51 is reflected from the test surface to produce beam 54, which is reflected by pellicle 50 into the objective of zoom lens 36 along with reference beam 52. The portion of beam 52 transmitted through pellicle 50 into the objective of zoom lens 36 interferes with reflected test beam 54 to produce interferogram beam 53.

Interferogram beam 53 is magnified by zoom lens 36 and transmitted as beam 55 to fold mirror 34, from which it is reflected as beam 56 to fold mirror 35, from which it is reflected as beam 57 into the aperture of CCD camera 33, which may be fitted with an optional 2X objective 36D. CCD camera 33 produces a suitable image signal 64 to drive monitor 30, which displays the interferogram 58 within the field of view, as shown in FIG. 1.

If the REF OUT button 26 on the front panel of interferometer unit 9 is deactuated, control circuit 48 removes a solenoid control signal 65 which was applied to solenoid 62. Solenoid 62, when released, thrusts a non-reflective member 63 into the path of beam 59, preventing it from being reflected by reference mirror 39. In this mode of operation, interferometer unit 9 simply functions as a zoom microscope, and displays the magnified surface of the optical fiber and/or optical connector surface being inspected.

During initial calibration of the interferometer, reference mirror 39 is adjusted using its theta/phi mount 40,41 to align return beam 52 with the optical axis 66 of zoom lens 36. (Although reference mirror 39 is nominally aligned to the optical axis 66 of zoom lens 36, its final adjustment compensates for any small misalignment of the nominal sample "yaw" and "pitch" positions. This ensures the same interferogram regardless of the random rotational orientation of the sample.)

After the test surface is properly mounted on a suitable chuck and thereby attached to bracket 22A,B of tilt stage 22 and with interferometer unit 9 in its "inspection mode" (with member 63 blocking beam 59) the optical fiber or connector end surface is positioned in the path of beam 51 at the focal point of zoom lens 36 by manipulating the x, y, and z micrometer controls 18, 16, and 20. As mentioned above, when optical fiber chuck 23A of FIG. 3A is utilized on the tilt stage 22 which is used in conjunction with optical fiber end surfaces, this is accomplished by manipulating the z control 20 to focus the visual image of vertical alignment surface 83B of alignment element 83 in a peripheral portion of the field of view of zoom lens 36.

It should be appreciated that when measuring fiber cleaves, and particularly angled fiber cleaves, it is much more difficult to ensure that the end surface of the optical fiber falls at the center of rotation 74 of pivot pin 60 to ensure that any tilt offset required does not disturb the xyz location of the sample. To resolve this problem the small reflective alignment element 83 visible in the peripheral portion of the field of view with zoom lens 36 in its "zoomed out" condition has been placed precisely in line with the axis of rotation 74. The operator therefore initially focuses on reflective alignment surface 83B before loading fiber 68 onto fiber chuck 23A such that is protrudes beyond reflective alignment surface 83B. The "nominal" or expected cleave angle (if any) of fiber 68 is set on tilt stage 22 by means of micrometer 42. The user then, without further adjustment of z control 20, slowly pulls back fiber 68 toward the surface 83B until a clear focused image of the fiber end is seen. In the case of angled cleaves, the fiber is rotated to optimize the visibility of its end surface. REF OUT button 26 then is actuated to cause solenoid 62 to withdraw blocking member 63, so interferometer unit 9 operates in its "interferometric mode" to produce an interferogram beam 53. Interferogram beam 53 is magnified by zoom lens 36 and sensed by CCD camera 33, causing the interferogram fringes 58 to be displayed on monitor 30.

The operator then adjusts z micrometer control knob 20 slightly to achieve maximum fringe contrast of fringes 58, and then operates ZOOM IN button 24 and/or ZOOM OUT button 25 to cause the optimum number of fringes to appear on monitor 30, and simultaneously controls the intensity of LED 37 to maintain adequate illumination of the fiber or connector end test surface.

Tilt stage 22 is pivotally connected by pivot pin 60 to the horizontal mounting surface of mounting plate 82, which in turn is securely attached to the top of x stage of xyz assembly 12. As described, the sample chucks 23A and 23 of FIGS. 3A and 3B are designed such that the end of the sample, that is, the end surface of the optical fiber 68 or optical connector 67 being inspected, is placed at the center axis 74 of pivot pin 60. The center axis 74 therefore is inherently adjusted by z micrometer 20 to be located at the focal point of zoom lens 36 during the initial measurement sequence described above.

This arrangement eliminates offset in the x direction during tilting of the sample chuck 23 or 23A (by rotating micrometer 42). With connector chuck 23 mounted on the vertical mounting surface at the bottom of recess 22C of tilt stage 22, the tilt orientation of the end surface of the ferrule 72 of optical connector 67 to be inspected is controlled by micrometer 42. Micrometer 42 is calibrated in degrees of "tilt" off the optical axis of chuck 23 or 23A relative to beam 51. In FIGS. 3A and 3B, arc 76 indicates the range of tilt of tilt stage 22 about vertical axis 74 through the center of pivot pin 60. Micrometer 42 and pivot stage assembly 22 are designed to adjust such tilt accurately between 0 and 15 degrees. Arc 44 (FIG. 2) indicates pivoting of tilt stage 22 in response to movements of micrometer thrust member 43B of arrows 43 in response to rotation of micrometer 42.

When measuring angled samples, the nominal or expected angle of the sample is set on the calibrated scale of micrometer 42. The sample then is axially rotated with interferometer unit 9 set to its inspection or microscope mode until the sample surface appears clearly on the monitor 30. Then interferometer unit 9 is set to its interference mode by actuating REF OUT switch 27, and the angle of tilt stage 22 is adjusted until the minimum number of fringes 58 appear on monitor 30, and the angle of the fiber or connector end surface then appears on the calibration scale of micrometer 42. This use of tilt stage 22 is essential where angled polishes, cuts or cleaves have been made in an optical fiber or the test surface of an optical connector is beveled, to minimize reflections.

The above described optical fiber/connector inspection and measurement system has been shown to provide greatly improved accuracy in measurement and evaluation of the topography of the end surface of an optical fiber or optical connector because of its ability to provide all available fringes across any selected area of the optical fiber/connector end surface, regardless of the curvature or slope of that area. Any desired "off axis" area of the end surface can be easily selected by using the zoom controls to change the magnification and using the precise x and y controls of the xyz stage. The ability to easily and precisely shift the axial orientation of the optical fiber/connector (relative to the z axis) and zoom in to an optimum magnification of the selected area allows fast, convenient evaluation of samples. Any magnification within the range of zoom lens 36 can be very rapidly selected, without correction of commercial overshoot, and without "losing focus" and hence avoiding any need for time-consuming readjustment of focus or lateral shift of the image.

When measuring spherically polished FC-PC style connectors of the type shown in FIG. 3B, concentric ring patterns will be produced that indicate both the center and the radius of curvature of the end surface. The parfocal/parcentral zoom capability of zoom lens 36 ensures that the image path and reference path remain in focus throughout the zoom range. The user may easily switch between the inspection (i.e. microscope) mode and interference mode at any magnification without refocusing, so details and imperfections of the end surface that might be missed with prior art devices using multiple fixed objectives are easily, quickly, and conveniently captured by the system of the present invention. Using various chucks, the described system can inspect and measure end surfaces of any single optical fiber, optical connector, or ribbon optical fiber.

The tilting operation of the chuck mounted on tilt stage 22 also facilitates the measurement of angled fiber cleaves, angled connectors, and also two serious defects known to occur in many "straight" or "angled" connectors, called "protrusion" or "undercut". Protrusion is a condition whereby the fiber protrudes beyond the polished surface of the ferrule. When physically mated with another connector the protruding fiber can be damaged, reducing performance of the optical system. Undercut is a far more likely defect, as the fiber generally wears faster than the ferrule during the polishing process. With undercut, the fiber is very slightly recessed below the ferrule surface. When two connectors are joined, a small air gap results. This air gap can lead to increased attenuation and reduced system bandwidth.

The fact that all optical surfaces of the described system are vertical and enclosed within a housing 55 prevents most dust from settling on the various optical surfaces, avoiding the need for frequent cleaning. Very substantial improvement in speed and accuracy of evaluating end surfaces of optical fiber/connectors over prior art devices in which only one or a few discrete magnifications are available in the inspection and/or interference modes are achieved by the present invention.

While the invention has been described with reference to several particular embodiments thereof, those skilled in the art will be able to make various modifications to the described embodiments of the invention without departing from the true spirit and scope of the invention. It is intended that all combinations of elements and steps which perform substantially the same function in substantially the same way to achieve the same result are within the scope of the invention. For example, another type of interferometer than a Michelson interferometer, for example a Twyman-Green interferometer, could be used. A laser light source could be used instead of the described LED 37. Alternatively, a higher or lower order magnification zoom lens could be used, and the different magnification might be compensated for by adding additional optics or changing the CCD element size of camera 33. By connecting an external computer, such as an IBM PC or compatible unit, equipped with a "frame grabber", interface printed circuit board, and fringe analysis/control software to the interface provided on the rear panel of interferometer unit 9, the external computer could automatically operate the interferometer unit and capture and display sample images and/or interferograms and compute therefrom information about the topography of the sample surface.

What is claimed is:

1. A method of using an evaluation device including an interferometer to evaluate the topography of an end surface of an optical fiber or optical connector, the interferometer including a light source, a beam splitter, a reference surface, and a CCD camera coupled to a display monitor, the method comprising the steps of:

(a) supporting the optical fiber or optical connector on an xyz stage;

(b) setting the interferometer to operate in a microscope mode;

(c) adjusting a z control of the xyz stage to move the end surface to a focal point of a parfocal, parcentral zoom lens included in the interferometer, and adjusting x and y controls of the xyz stage to align an image of the end surface displayed on the monitor within the field of view of the zoom lens;

(d) setting the interferometer to operate in an interference mode to cause a fringe pattern resulting from interference of a test beam reflected from the end surface with a reference beam reflected from the reference surface to be displayed on the monitor;

(e) adjusting the z control to optimize the contrast of the displayed fringe pattern; and (f) operating the zoom lens to change magnification of the fringe pattern to obtain a desired number of available fringes across a selected portion of the end surface without refocusing or realigning the end surface with the focal point of the zoom lens.

2. The method of claim 1 wherein the light source includes a light emitting diode, the method including adjusting the intensity of a beam emitted by the light emitting diode to improve the visibility of the displayed fringe pattern as the magnification is changed in step (f).

3. The method of claim 1 wherein the interferometer includes a tilt stage supporting the optical fiber or optical connector, the end surface having an angle in the range of 0 to 15 degrees relative to a plane perpendicular to a longitudinal axis of the optical fiber or optical connector at the end surface, the method including, after the adjusting of the z control to move the end surface to the focal point, adjusting the angle of the tilt stage to an approximate value of the angle of the end surface, and rotating the optical fiber or optical connector to optimize visibility of the end surface on the monitor.

4. A method of using an evaluation device including an interferometer to evaluate the topography of an end surface of an optical fiber or optical connector, the interferometer including a light source, a beam splitter, a reference surface, and a CCD camera coupled to a display monitor, the method comprising the steps of:

(a) supporting the optical fiber or optical connector on an xyz stage;

(b) setting the interferometer to operate in a microscope mode;

(c) adjusting a z control of the xyz stage to move the end surface to a focal point of a parfocal, parcentral zoom lens included in the interferometer, and adjusting x and y controls of the xyz stage to align an image of the end surface displayed on the monitor within the field of view of the zoom lens;

(d) setting the interferometer to operate in an interference mode to cause a fringe pattern resulting from interference of a test beam reflected from the end surface with a reference beam reflected from the reference surface to be displayed on the monitor;

(e) adjusting the z control to optimize the contrast of the displayed fringe pattern;

(f) operating the zoom lens to change magnification of the fringe pattern to obtain a desired number of available fringes across a selected portion of the end surface without refocusing or realigning the end surface with the focal point of the zoom lens, wherein the interferometer includes a tilt stage supporting the optical fiber or optical connector;

(g) adjusting an angle of the tilt stage to measure a bevel angle of the end surface without substantial adjustment of the xyz stage to refocus the end surface or align it with the focal point of the zoom lens.

5. A method of using an evaluation device including an interferometer to evaluate the topography of an end surface of an optical fiber or optical connector, the interferometer including a light source, a beam splitter, a reference surface, and a CCD camera coupled to a display monitor, the method comprising the steps of:

(a) supporting the optical fiber or optical connector on an xyz stage;

(b) setting the interferometer to operate in a microscope mode;

(c) adjusting a z control of the xyz stage to move the end surface to a focal point of a parfocal, parcentral zoom lens included in the interferometer, and adjusting x and y controls of the xyz stage to align an image of the end surface displayed on the monitor within the field of view of the zoom lens;

(d) setting the interferometer to operate in an interference mode to cause a fringe pattern resulting from interference of a test beam reflected from the end surface with a reference beam reflected from the reference surface to be displayed on the monitor;

(e) adjusting the z control to optimize the contrast of the displayed fringe pattern; and (f) operating the zoom lens to change magnification of the fringe pattern to obtain a desired number of available fringes across a selected portion of the end surface without refocusing or realigning the end surface with the focal point of the zoom lens, wherein the interferometer includes a tilt stage supporting the optical fiber or optical connector, wherein the adjusting of the z control to move the end surface to the focal point includes optimizing the focus of a reflective alignment surface on the tilt stage and located in precise alignment with a pivot axis of the pivot stage.

6. The method of claim 5 wherein the end surface of the optical fiber has an angle in the range of 0 to 15 degrees relative to a plane perpendicular to a longitudinal axis of the optical fiber at the end surface, the method including alignment of the end surface with the reflective alignment surface, adjusting of the angle of the tilt stage to an approximate value of the angle of the end surface, and rotating the optical fiber to optimize visibility of the end surface on the monitor.

7. A method of using an evaluation device including an interferometer to evaluate the topography of an end surface of an optical fiber or optical connector, the interferometer including a light source, a beam splitter, a reference surface, and a CCD camera coupled to a display monitor, the method comprising the steps of:

(a) supporting the optical fiber or optical connector on an xyz stage;

(b) adjusting a z control of the xyz stage to move the end surface to a focal point of a parfocal, parcentral zoom lens included in the interferometer, and adjusting x and y controls of the xyz stage to align an image of the end surface displayed on the monitor within the field of view of the zoom lens, the interferometer causing a fringe pattern resulting from interference of a test beam reflected from the end surface with a reference beam reflected from the reference surface to be displayed on the monitor;

(c) adjusting the z control to optimize the contrast of the displayed fringe pattern; and (d) operating the zoom lens to change magnification of the fringe pattern to obtain a desired number of available fringes across a selected portion of the end surface without refocusing or realigning the end surface with the focal point of the zoom lens.

8. A device for inspecting and/or evaluating an end surface of an optical fiber or optical connector, including an interferometer having a light source, a beam splitter, a reference surface, and a CCD camera coupled to a display monitor, the inspection device comprising in combination:

(a) an xyz stage;

(b) a chuck supporting the optical fiber or optical connector on the xyz stage;

(c) a beam blocking element selectively operable to block a beam in a reference arm of the interferometer to set the interferometer in a microscope mode;

(d) a parfocal, parcentral zoom lens in the interferometer;

(e) a z control of the xyz stage operable to move the end surface to a focal point of the zoom lens;

(f) x and y controls of the xyz stage operable to align an image of the end surface displayed on the monitor within the field of view of the zoom lens;

(g) means for setting the interferometer to operate in an interference mode to cause a fringe pattern resulting from interference of a test beam reflected from the end surface with a reference beam reflected from the reference surface to be displayed on the monitor, whereby the z control can be operated to optimize the contrast of the displayed fringe pattern; and (h) zoom in and zoom out controls for operating the zoom lens to change magnification of the fringe pattern to obtain all of an available number of fringes across a selected portion of the end surface without refocusing or realigning the end surface with the focal point of the zoom lens, whereby maximum resolution of features of the selected portion of the end surface can be determined from the fringes.

9. The device of claim 8 including an intensity control circuit for adjusting the intensity of a beam emitted by the light source to improve the visibility of the displayed fringe pattern as the magnification is changed.

10. A device for inspecting and/or evaluating an end surface of an optical fiber or optical connector, including an interferometer having a light source, a beam splitter, a reference surface, and a CCD camera coupled to a display monitor, the inspection device comprising in combination:

(a) an xyz stage;

(b) a chuck supporting the optical fiber or optical connector on the xyz stage;

(c) a beam blocking element selectively operable to block a beam in a reference arm of the interferometer to set the interferometer in a microscope mode;

(d) a parfocal, parcentral zoom lens in the interferometer;

(e) a z control of the xyz stage operable to move the end surface to a focal point of the zoom lens;

(f) x and y controls of the xyz stage operable to align an image of the end surface displayed on the monitor within the field of view of the zoom lens;

(g) means for setting the interferometer to operate in an interference mode to cause a fringe pattern resulting from interference of a test beam reflected from the end surface with a reference beam reflected from the reference surface to be displayed on the monitor, whereby the z control can be operated to optimize the contrast of the displayed fringe pattern;

(h) zoom in and zoom out controls for operating the zoom lens to change magnification of the fringe pattern to obtain all of an available number of fringes across a selected portion of the end surface without refocusing or realigning the end surface with the focal point of the zoom lens, whereby maximum resolution of features of the selected portion of the end surface can be determined from the fringes; and (i) a tilt stage supported in pivotal relationship to the xyz stage about a rotational axis and supporting the optical fiber or optical connector and a tilt control for adjusting an angle of the tilt stage to measure an angle of the end surface without substantial adjustment of the xyz stage to refocus the end surface or align it with the focal point of the zoom lens.

11. A device for inspecting and/or evaluating an end surface of an optical fiber or optical connector, including an interferometer having a light source, a beam splitter, a reference surface, and a CCD camera coupled to a display monitor, the inspection device comprising in combination:

(a) an xyz stage;

(b) a chuck supporting the optical fiber or optical connector on the xyz stage;

(c) a beam blocking element selectively operable to block a beam in a reference arm of the interferometer to set the interferometer in a microscope mode;

(d) a parfocal, parcentral zoom lens in the interferometer;

(e) a z control of the xyz stage operable to move the end surface to a focal point of the zoom lens;

(f) x and y controls of the xyz stage operable to align an image of the end surface displayed on the monitor within the field of view of the zoom lens;

(g) means for setting the interferometer to operate in an interference mode to cause a fringe pattern resulting from interference of a test beam reflected from the end surface with a reference beam reflected from the reference surface to be displayed on the monitor, whereby the z control can be operated to optimize the contrast of the displayed fringe pattern;

(h) zoom in and zoom out controls for operating the zoom lens to change magnification of the fringe pattern to obtain all of an available number of fringes across a selected portion of the end surface without refocusing or realigning the end surface with the focal point of the zoom lens, whereby maximum resolution of features of the selected portion of the end surface can be determined from the fringes;

(i) a tilt stage supported in pivotal relationship to the xyz stage about a rotational axis and supporting the optical fiber or optical connector; and (j) a reflective alignment surface on the tilt stage located in precise alignment with the rotational axis, the reflective alignment surface being located adjacent to but not touching the end surface of the optical fiber or optical connector, whereby the rotational axis can be aligned with the focal point by adjusting the z control to optimize focus of the reflective alignment surface on the monitor.

12. A device for inspecting and/or evaluating an end surface of an optical fiber or optical connector, including an interferometer including a light source, a beam splitter, a reference surface, and a CCD camera coupled to a display monitor, the inspection device comprising in combination:

(a) an xyz stage;

(b) a chuck supporting the optical fiber or optical connector on the xyz stage;

(c) a parfocal, parcentral zoom lens in the interferometer;

(d) a z control of the xyz stage operable to move the end surface to a focal point of the zoom lens;

(e) x and y controls of the xyz stage operable to align an image of the end surface displayed on the monitor within the field of view of the zoom lens;

(f) means for operating the interferometer in an interference mode to cause a fringe pattern resulting from interference of a test beam reflected from the end surface with a reference beam reflected from the reference surface to be displayed on the monitor, whereby the z control can be operated to optimize the contrast of the displayed fringe pattern; and (g) zoom in and zoom out controls for operating the zoom lens to change magnification of the fringe pattern to obtain all of an available number of fringes across a selected portion of the end surface without refocusing or realigning the end surface with the focal point of the zoom lens, whereby maximum resolution of features of the selected portion of the end surface is determinable from the fringes.

13. A device for inspecting and/or evaluating an end surface of an optical fiber or optical connector, including an interferometer having a light source, a beam splitter, a reference surface, and a CCD camera coupled to a display monitor, the inspection device comprising in combination:

(a) an xyz stage;

(b) a chuck supporting the optical fiber or optical connector on the xyz stage;

(c) a lens in the interferometer;

(d) a z control of the xyz stage operable to move the end surface to a focal point of the lens;

(e) x and y controls of the xyz stage operable to align an image of the end surface displayed on the monitor within the field of view of the lens;

(f) means for setting the interferometer to operate in an interference mode to cause a fringe pattern resulting from interference of a test beam reflected from the end surface with a reference beam reflected from the reference surface to be displayed on the monitor, whereby the z control can be operated to optimize the contrast of the displayed fringe pattern; and (g) a tilt stage supported in pivotal relationship to the xyz stage about a rotational axis and supporting the optical fiber or optical connector and a tilt control for adjusting an angle of the tilt stage to measure an angle of the end surface without substantial adjustment of the xyz stage to refocus the end surface or align it with the focal point of the lens.

14. The device of claim 13 further including a beam blocking element selectively operable to block a beam in a reference arm of the interferometer to set the interferometer in a microscope mode.

* * * * *